United States Patent [19]
Willems

[11] 3,962,444
[45] June 8, 1976

[54] USE OF 4-THIOCYANO-QUINAZOLINES AS FUNGICIDES

[75] Inventor: Antonius Gerhardus Maria Willems, van Houtenlaan, Netherlands

[73] Assignee: U.S. Philips Corporation, New York, N.Y.

[22] Filed: Mar. 19, 1975

[21] Appl. No.: 559,823

Related U.S. Application Data

[62] Division of Ser. No. 384,685, Aug., 1973, Pat. No. 3,888,857.

[30] Foreign Application Priority Data

Aug. 9, 1972 Netherlands.................... 7210866

[52] U.S. Cl.................................. 424/251; 424/18; 424/45; 424/168
[51] Int. Cl.² .................... A01N 9/22; A01N 17/00; A01N 17/10
[58] Field of Search ............... 424/251, 18, 45, 168

[56] References Cited
OTHER PUBLICATIONS
Smith, P.A.S., "Open–Chain Nitrogen Compounds," vol. 1, W. A. Benjamin, Inc., (1965), p. 245.

Primary Examiner—Jerome D. Goldberg
Assistant Examiner—Allen J. Robinson
Attorney, Agent, or Firm—Frank R. Trifari; Norman N. Spain

[57] ABSTRACT

Thiocyano quinazolines of the formula

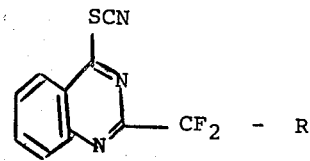

where R is fluoro or difluoromethyl are useful for combatting plant harmful fungi infections.

4 Claims, No Drawings

USE OF 4-THIOCYANO-QUINAZOLINES AS FUNGICIDES

This is a division, of application Ser. No. 384,685, filed Aug. 1, 1973 and now U.S. Pat. No. 3,888,857.

The invention relates to two new substances which comply with the following formula:

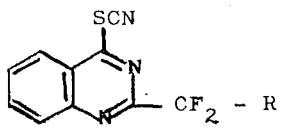

in which R denotes a fluorine atom or a difluoromethyl group.

The substances according to the invention exhibit a substantial fungicidal activity against fungi which occur in agricultural and horticultural plants as well as against the *terrricolous* fungi *Rhizoctonia solani* and *Pythium sp*. On the basis of their activity the compounds according to the invention, after being worked up into preparations, can be used for controlling and preventing fungi infection in agricultural and horticultural plants and for soil desinfection.

More specifically, it has been found that the following parenthesized plants, after being treated with the compounds according to the invention, are adequately protected against infection by the fungi species listed before each plant *Pirricularia oryzane* (rice), *Helminthosporium oryzae* (rice), *Venturia inaequalis* (apple), *Phytophotora infestans* (inter alia, potato and tomato) and *Erysiphe cichocaraccarum infestans* (squash).

Furthermore, it has been found that the compounds according to the invention have a curative activity with respect to fungi infections on apple caused by *Venturia inaequalis*. This last mentioned biological aspect is highly interesting because by a virtue of this activity the compounds according to the invention may constitute a substitute for the mercury compounds which until recently were frequently used for controlling *Venturia inaequalis* infections. The mercury compounds are highly toxic and in many countries their use is prohibited or subject to stringent restrictions.

Another important biological aspect of the compounds according to the invention is the fungicidal activity against both *Piricularia oryzae* and *Helminthosporium orayzae*. Both fungi frequently occur together on rice. Treatment of rice with the compounds according to the invention yields the favorable result that this plant is protected against infection by either and by both fungi.

The fungicidal activity mentioned hereinbefore has been found in a biological evaluation test in which, inter alia, the following test methods have been used:

1. Test for preventive activity against plant infection by *Piricularia oryzae* and *Helminthosporium oryzae*.

Rice of the "Maratelli" variety is sowed in the glasshouse in small plastic pots each containing 75 ml of humous potting soil. The pots are placed in a plant bed, the temperature of which is maintained at approximately 27°C. The potting soil is treated with a fertilizer solution and after a fortnight the plants developing from the seed are sprayed with aqueous dispersions of the compounds according to the invention in different concentrations. The plants thus treated are subsequently infected with *Piricularia oryzae* or *Helminthosporium oryzae* by spraying the plants with an aqueous suspension which contains 200,000 spores of *Piricularia oryzae* or *Helminthosporium oryzae* per ml. After an incubation period of 5 days at a temperature of 23°–25° C and a relative humidity of 100 percent it is ascertained if and to which extent the fungi have developed.

2. Test for preventive action with respect to plant infection by *Venturia inaequalis*.

Apple seedlings are sprayed with an aqueous dispersion of the compounds according to the invention in different concentration. The liquid thus applied is allowed to dry and subsequently the apple seedlings are infected with a suspension of spores of *Venturia inaequalis*. After an incubation period of 2–3 weeks at a temperature of 18° C and a relatively humidity of 100 percent it is ascertained whether the mould has developed and if so to what extent.

3. Test for curative action with respect to plant infection caused by *Venturia inaequalis*.

This test largely corresponds to that described previously in two, but with the difference that now the apple seedlings are first infected and subsequently, after 48 hours, treated with the aqueous suspensions of the compounds according to the invention.

4. Test for the duration of the preventive action with respect to plant infestation by *Venturia inaequalis*.

This test largely corresponds to that described under two, with the proviso that the apple seedlings are now infected with the spore suspension 48 hours after they have been sprayed with the aqueous dispersion of the substances according to the invention.

5. Test for preventive action with respect to plant infestation by *Phytophtora infestans*.

From 3-week tomato plants of the "Bonny Best," variety, which have four leaves, the two lower leaves are removed. The plants are sprayed with an aqueous dispersion of the compounds according to the invention in varying concentrations. Subsequently, the plants are infected with *Phytophtora infestans* by spraying the plants with an aqueous suspension which contains 100,000 zoospores of *Phytophtora infestans* per ml. After an incubation period of 4 days at a temperature of 15°–18° C and a relative humidity of 100 percent it is ascertained whether the applied fungi have developed and to what extent.

6. Test for activity with respect to *terricolores* fungi.

a. Test for activity with respect to *Rhizoctonia solani*.

The substances according to the invention are mixed with non-sterilized soil and subsequently the soil is infected with an amount of a pulverized shaking culture of Rhizoctonia solani. Pieces of flax straw of approximately 5 cm length are vertically inserted in the soil. After 24 hours the straws are rinsed with tap water and are arranged horizontally on a 2 percent agar medium which contains 1 p.p.m. (part per million) of terrazole. Twenty-four hours later it is ascertained whether *Rhizoctonia solani* have developed around the straw.

b. Test for activity with respect to *Pythium sp*.

The substances according to the invention are mixed with non-sterilized soil which is naturally infected with *Pythium Sp*. Sterilized grains, which have been soaked in water, are brought underneath the surface of the soil. After 24 hours the grains are rinsed with tap water and are placed on a 2 percent agar medium which contains 10 p.p.m. of benomyl. Twenty-four hours later it is ascertained whether mould growth has taken place around the grains.

The results of these biological tests are as follows.

A satisfactory protection of rice against infestation by *Piricularia oryzae* is obtained if rice is treated with an aqueous dispersion of the substances according to the invention, the dispersion containing approximately 0.1 g of the active substance per liter. Treating rice with an aqueous dispersion which contains 0.3 g of the active substance per liter affords adequate protection against infestation by *Helminthosporium oryzae*. Protection of plants such as tomato against infestation by *Phytophthora intestans* is obtained by treatment with an aqueous dispersion which contains approximately 0.3 g of the active substance.

When used preventively on apple satisfactory protection against infestation by *Venturia inaequalis* is obtained if the plant is sprayed with an active dispersion which contains 0.03 – 0.3 g of the substance according to the invention per liter. Forty-eight hours after spraying the protection is still adequate. For the curative use of the substances according to the invention with respect to *Venturia inaequalis* infections on apple satisfactory results are obtained if the infected plant is sprayed with a watery dispersion which contains approximately 0.2 – 0.5 g of the active substance per liter.

Furthermore, the substances according to the invention in a dosage of 10 kg per hectare and more are useful for controlling *terricolous* fungi.

For practical use the substances according to the invention are processed into preparations containing them. In such preparations the active substance is mixed with a solid carrier or dissolved or dispersed in a liquid carrier, if desired in combination with adjuvants, such as surface-active substances and stabilizers. Examples of preparations according to the invention are aqueous dispersions, oil solutions and oil dispersions, solutions in organic solvents, pastes, dusts, wettable powders, miscible oils, granules, invert emulsions, aerosol preparations and fumigating candles.

Wettable powders, pastes and miscible oils are preparations in concentrated form which are diluted with water before or during use.

Invert emulsions and solutions in organic solvents are mainly used for air application, namely when large areas are treated with a comparatively small amount of preparation. The invert emulsions can be prepared by emulsifying water in an oil solution or an oil dispersion of the active substance in the spraying apparatus shortly before or even during spraying. Solutions of the active substance in organic solvents such as isophoron, hexamethylphosphorphoric acid triamide, dimethyl formamide and dodecyl benzene may be provided with a phytotoxity-reducing substance such as wool grease, wool grease acid or wool grease alcohol. Hereinafter, some formulations, given by way of example, are described in more detail.

Granular preparations are produced, for example, by absorbing the active substance in a solvent, the resultant solution, as the case may be in the presence of a binder, being used to impregnate granular carrier material such as porous granules (for example pumice and attaclay), mineral non-porous granules (sand or ground marl), organic granules (for example coffee grounds and cur tobacco stems).

A granular preparation may alternatively be produced by compressing the active substance together with powdered minerals in the presence of lubricants and binders, the pressings being disintegrated and strained to the desired grain size.

Dusts are obtainable by intimately mixing the active substance with an inert solid carrier material, for example in a concentration of 1 to 50 percent by weight. Examples of suitable solid carrier materials are talc, kaolin, pipe clay, diatomite earth, dolomite, gypsum, chalk, bentonite, attapulgite and colloidal $SiO_2$ or mixtures of these and similar substances. Organic carrier materials such as, for example ground walnut shells may also be used.

Wettable powders may be prepared by mixing from 10 to 80 parts by weight of a solid inert carrier such as, for example one of the above-mentioned carrier materials, with from 10 to 80 parts by weight of the active substance, from 1 to 5 parts by weight of a dispersing agent such as, for example, the lignin sulphonates or alkyl naphthalene sulphonates known for this purpose, and preferably also from 0.5 to 5 parts by weight of a wetting agent such as fatty alcohol sulphates, alkylaryl sulphonates or fatty-acid condensation products.

For the production of miscible oils the active compound is dissolved, or finely divided, in a suitable solvent, which preferably is poorly miscible with water, an emulsifier being added to said solution. Suitable solvents are, for example, xylene, toluene, high-aromatic petroleum distillates, for example solvent naphtha, distilled tar oil and mixtures of these liquids. Suitable emulsifying agents are for example, alkyl phenoxypolyglycol ethers, polyoxyethylene sorbitan esters of fatty acids or polyoxyethylene sorbitol esters of fatty acids. The concentration of the active compound in these miscible oils is not restricted within narrow limits and may vary between 2 and 50 percent by weight. In addition to a miscible oil there may be mentioned as a liquid and highly concentrated primary composition a solution of the active substance in a liquid which is satisfactorily miscible with water, for example acetone, to which solution a dispersing agent and, as the case may be, a wetting agent is added. On dilution with water shortly before or during spraying an aqueous dispersion of the active substance is obtained.

An aerosol preparation according to the invention is obtained in the usual manner by incorporating the active substance, if required in the form of a solution, in a volatile liquid to be used as a propellant such as for example, a mixture of chlorine and fluorine derivatives of methane and ethane.

Fumigating candles or fumigating powders, i.e., preparations which are capable of developing a pesticidal smoke when burning, are obtained by absorbing the active substance in a combustible mixture which for example, may contain a sugar or wood, preferably in ground form, a substance to maintain combustion such as, for example ammonium nitrate or potassium chlorate, and further a substance to retard combustion, for example kaolin, bentonite and/or colloidal silicic acid.

In addition to the above mentioned ingredients the preparations according to the invention may contain further substances which are known for use in such preparations.

For example to a wetting powder or a mixture to be granulated a lubricant such as a calcium or magnesium stearate may be added. Also "adhesives" such as polyvinyl alcohol cellulose derivatives or other colloidal materials such as casein, may be added to improve the adherence of the pesticide to the plant to be treated.

Further, pesticidal compounds which are known per se may be included in the preparations according to the invention. This ensures that the spectrum of activity of the preparation is widened and synergism may be obtained.

The following insecticidal fungicidal acaricidal compounds, known per se, are suitable for inclusion in such a combination preparation.

Insecticides such as:
1. chlorinated hydrocarbons, for example 2,2-bis (p-chlorophenyl)-1,1,1-trichloro ethane and hexachloroepoxy-octahydro-dimethanonaphthalene;
2. carbonates, for example N-methyl-1-naphthyl-carbamate;
3. dinitrophenols, for example 2-methyl-4,6-dinitrophenol and 2-(butyl)-4,6-dinitrophenyl 3,3-dimethylacrylate;
4. organic phosphorus compounds, such as dimethyl-2-methoxy-carbonyl-1-methylvinyl-phosphate; O,O-diethyl-O-p.nitrophenyl phosphorthioate; N-monomethylamide of O,O-dimethyl-dithiophosphoryl acetic acid;

Acaricides such as:
1. diphenylsulphides, for example p-chloro benzyl-p-chlorophenyl sulphide and 2,4,4'-5-tetrachloro diphenylsulphide;
2. diphenylsulfonates, for example p-chlorophenyl benzene sulphonate;
3. methyl carbinols, for example 4,4-dichloro-a-trichloromethyl benzhydrol;
4. quinoxaline compounds such as methyl quinoxaline dithiocarbonate.

Fungicides such as:
1. organic tin compounds, for example, triphenyl-tin hydroxide and triphenyl tin acetate;
2. alkylene bisdithio-carbamates, for example zinc ethylene bisdithio-carbamate and manganese ethylene bisdithiocarbamate;
3. and further 2,4-dinitro-6-(2-octyl-phenylcrotonate), 1- [bis(dimethylamino)phosphoryl] -3-phenyl-5-amino-1,2,4-triazole, 6-methyl-quinoxaline-2,3-dithiocarbonate, 1,4-dithioantraquinone-2,3-dicarbonitrile.

N-trichloro-methyl thiophthalimide,
N-trichloromethyl thiotetrahydrophthalimide,
N-(1,1,2,2-tetrachloroethylthio)-tetrahydrophthalimide,
N-dichloro fluoromethylthio-N-phenyl-N'-dimethyl-sulphonyl-diamide and tetrachloro isophthalonitrile.

For practical use the desired dosage of the preparation according to the invention will depend inter alia, on the selected active substance, the preparation formulation, the plant species to be protected against infestation by fungi, the mould species to be controlled, the condition of the cultivated plants and the conditions of wheather.

In general favorable results are obtained with a dosage corresponding to from 0.03 to 1 kg of the active substance per hectare.

The substances according to the invention are novel compounds which may be produced by methods, which are known per se, for the synthesis of similar substances, or which are analogous thereto.

For example, the substances according to the invention may be prepared by treating a compound of the formula:

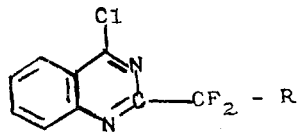

where R is a fluorine atom or a difluoromethyl group, with a metal thiocyanate. The reaction is carried out in the presence of an acid binder such as for example in acetic acid or crystalline acetic acid. The reaction temperature approximtely equals room temperature. A suitable metal thiocyanate is potassium thiocyanate.

For the synthesis of the starting substances reference is made to the examples.

EXAMPLES

1. Preparation of 2-trifluoromethyl-4-thiocyano-quinazoline a. Preparation of 2-trifluoromethyl-quinazoline-4 (3H)-one.

68 g of anthranilamide which is obtained by reacting isatoic acid anhydride with ammonium hydroxide is dissolved in 350 ml of acetonitrile. At a temperature of 70°C 107 g of trifluoroacetic acid anhydride is added to the solution thus obtained. The reaction mixture is stirred for 2 hours at 70°C and subsequently poured into 1.5–2 l of water. The resulting precipitate is drawn off, dissolved in 350 ml of 2N-caustic soda solution and hot-filtered after adding activated carbon chloride. The filtrate is acidified with approximately 100 ml of concentrated hydrochloric acid. The resultant precipitate is drawn off and washed with water. The 2-trifluoromethyl-quinazoline-4(3H)-on thus obtained has a melting point of 220°C with decomposition.

b. Preparation of 2-trifluoromethyl-4-chloro-quinazoneline 47.5 g of sodium metabisulphite and 120 g of 2-trifluoromethyl-quinazoline-4(3H)-on are added to 265 ml of phosphorus oxychloride. The mixture is refluxed until no more HCl escapes. The excess phosphorus oxychloride is distilled off and the residue is taken up in 400 ml of dry toluene. While stirring the resulting substance is poured into 1 l of ice water, stirring being continued for 20 minutes. The toluene layer is separated from the water layer, the latter being extracted twice with toluene. The common toluene layers are washed with water after which the toluene is distilled off. The 2-trifluoro-methyl-4-chloroquinazoline thus obtained has a melting point of 61°–62°C.

c. Preparation of 2-trifluoromethyl-4-thiocyano-quinazoline.

46.5 g of 2-trifluoromethyl-4-chloro-quinazoline is added, while stirring, to a mixture of 97 g of potassium-thiocyanate and 200 ml of acetic acid. The reaction mixture is stirred for 2 hours at room temperature, the resultant light-yellow precipitate is drawn off, consecutively washed with a small amount of acetic acid and water and subsequently dried in air. The 2-trifluoromethyl-4-thiocyano-quinazoline thus obtained has a melting point of 134°–136°C.

2. Preparation of 4-thiocyano-2-(1,1,2,2-tetrafluoro ethyl)-quinazoline a. Preparation of 2-(1,1,2,2-tetrafluoropropionylamino)-benzamide 20.4 g of anthranilamide is dissolved in a mixture of 200 ml of dry acetonitrile and 21 ml of triethylamine. Whilst stirring and at a temperature of 20°–25°C 25 g of 1,1,2,2-tetrafluoro propionyl chloride is added. The resultant mixture is stirred for another 30 minutes and evaporated in vacuo. Consecutively, the residue is washed with 2N HCl and water and finally dried. The resultant 2-(1,1,2,2-tetrafluoro propionylamino)-benzamide has a melting point of 115°C after recrystallisation from benzene.

b. Preparation of 2-(1.12.2-tetrafluoroethyl)-quinazoline-4(3H)-one.

15 g of 2-(1,1,2,2-tetrafluoropropionylamino)-benzamide is dissolved in 60 ml of 2N NaOH and the solution is heated for 1 hour under a reflux condenser. The reaction mixture is cooled down to 40°C, acidified with 2N HCl and subsequently cooled to room temperature. The resultant precipitate is drawn off, washed with water and dried to constant weight at 120°C. The melting point of the resulting 2-(1,1,2,2-tetrafluoroethyl)-quinazoline-4-(3H)-on is 196°–197.5°C.

c. Preparation of 4-chloro-2-(1,1,2,2-tetrafluoroethyl-quinazoline 12.8 g of 2-(1,1,2,2-tetrafluoroethyl)-quinazoline-4-(3H)-on and 13.8 g of phosphorus pentachloride are boiled for 5 hours in 50 ml of phosphorus oxychloride under a reflux condenser. The excess of phosphorus oxychloride is evaporated in vacuo and the residue is taken up in ice water. The resultant precipitate is drawn off, washed with water and dried in vacuo. The resulting 4-chloro-2-(1,1,2,2-tetrafluoro ethyl)-quinazoline has a melting point of 52°–53°C.

d. Preparation of 4-thiocyano-2-(1,1,2,2-tetrafluoroethyl)-quinazoline 7.9 g of 4-chloro-2-(1,1,2,2-tetrafluoroethyl)-quinazoline are dissolved in 10 ml of glacial acetic acid and subsequently 4.9 g of potassium-thiocyanate are added to this solution. Whilst stirring at room temperature the potassium thiocyanate dissolves in approximately 1 hour. The solution is stirred for another 2 hours, a precipitation being obtained. This precipitation is drawn off, washed with water and dried in vacuo. After recrystallization from isoporpanol the resulting 4-thiocyano-2-(1,1,2,2-tetrafluoro-ethyl)-quinazoline has a melting point of 112°–114.5°C.

3. Wettable powders are made from the active substances according to the invention by mixing 25 percent by weight of the active substance with 3 percent by weight of calcium lignin sulphonate, 2 percent by weight of dibutylnaphthalene-sulphonate and 70 percent by weight of kaolin. For practical purposes the wettable powders thus obtained are dispersed in water to a concentration of 30–1000 p.p.m. (parts per million) of the active substance. The aqueous dispersion is subsequently sprayed over the plants to be protected or the infected plants in amounts of approximately 1000 l per ha.

I claim:

1. A fungicidal preparation comprising a fungicidally effective amount of a 4-thiocyano-quinazoline of the formula

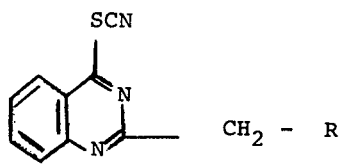

wherein R is a member selected from the group consisting of fluoro and difluoromethyl and a carrier therefore.

2. The fungicidal preparation of claim 1 wherein the carrier is a finely divided inert solid.

3. The fungicidal preparation of claim 1 wherein the carrier is an inert liquid.

4. A method of controlling fungi infections in agricultural and horticultural plants comprising treating the areas containing said plants with the fungicidal preparation of claim 1 in a dosage corresponding to 0.03 to 1 kg of said quinazoline per hectare.

* * * * *

UNITED STATES PATENT OFFICE
CERTIFICATE OF CORRECTION

Patent No. 3,962,444  Dated June 8, 1976

Inventor(s) Antonius Gerhardus Maria Willems

It is certified that error appears in the above-identified patent and that said Letters Patent are hereby corrected as shown below:

In the Title Page, Item [75], "van Houtenlaan" should read -- Weesp --.

Signed and Sealed this Sixteenth Day of November 1976

[SEAL]

Attest:

RUTH C. MASON
*Attesting Officer*

C. MARSHALL DANN
*Commissioner of Patents and Trademarks*